(12) United States Patent
Burke et al.

(10) Patent No.: US 9,365,621 B2
(45) Date of Patent: Jun. 14, 2016

(54) METHOD FOR PREVENTING NEOPLASTIC TRANSFORMATION BY INHIBITION OF RETINOBLASTOMA PROTEIN INACTIVATION

(71) Applicant: The Regents of the University of California, Oakland, CA (US)

(72) Inventors: Jason Burke, Santa Cruz, CA (US); Seth Rubin, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/394,203

(22) PCT Filed: Apr. 12, 2013

(86) PCT No.: PCT/US2013/036263
§ 371 (c)(1),
(2) Date: Oct. 13, 2014

(87) PCT Pub. No.: WO2013/155360
PCT Pub. Date: Oct. 17, 2013

(65) Prior Publication Data
US 2015/0259384 A1    Sep. 17, 2015

Related U.S. Application Data

(60) Provisional application No. 61/623,211, filed on Apr. 12, 2012.

(51) Int. Cl.
C07K 7/64    (2006.01)
C07K 7/06    (2006.01)
A61K 38/08   (2006.01)
A61K 38/00   (2006.01)

(52) U.S. Cl.
CPC . *C07K 7/64* (2013.01); *A61K 38/08* (2013.01); *C07K 7/06* (2013.01); *A61K 38/00* (2013.01)

(58) Field of Classification Search
None
See application file for complete search history.

(56) References Cited

U.S. PATENT DOCUMENTS 7,067,646 B2 *  6/2006  Nakatani ............ C07K 14/4736
                                                    435/320.1
2010/0143440 A1 *  6/2010  Prichard ............... A61K 31/366
                                                    424/423

OTHER PUBLICATIONS

Singh, M., et al, "Molecular Determinants for the Complex Formation between the Retinoblastoma Protein and LXCXE Sequences," The Journal of Biological Chemistry vol. 280, No. 45, pp. 37868-37876, Nov. 11, 2005.*

* cited by examiner

*Primary Examiner* — Thomas S Heard
(74) *Attorney, Agent, or Firm* — Adam Warwick Bell; Matthew Rupert Kaser (57) ABSTRACT

A method for preventing neoplastic transformation by inhibition of cell cycle progression into S phase by preventing the inactivation of Retinoblastoma protein (Rb).

3 Claims, 4 Drawing Sheets

SEQUENCE LISTING

All the below sequences are synthetic polypeptides

SEQ ID No.1 DLYCYEQLN

SEQ ID No.2 DLdYCdYEdQLN where dY and dQ are D-tyrosine and D-glutamine

SEQ ID No.3 DLYCYEQFN

SEQ ID No.4 EDLYCYEQLN

SEQ ID No.5 EDLdYCdYEdQLN where dY and dQ are D-tyrosine and D-glutamine

SEQ ID No.6 NLFCSEEMD

SEQ ID No.7 NLdFCdSEdEMD where dF and dS and dE are D-phenylalanine, Dseriene, and D-glutamate SEQ ID No.8 ELFCSEEMD SEQ ID No.9 ELFCSEEFD SEQ ID No.10 ELFCSEEMR SEQ ID No.11 PHpTPVRTVMATIQQLMMILN SEQ ID No.12 PHpTPVRTVMATIQ SEQ ID No.13 PEpTPVRTVMATIQQLMMILN SEQ ID No.14 PHpTPLRTVMATIQQLMMILN SEQ ID No.15 PHpTPVRTLMATIQQLMMILN FIG.4 (sequence listing)

MeTHOD FOR PREVENTING NEOPLASTIC TRANSFORMATION BY INHIBITION OF RETINOBLASTOMA PROTEIN INACTIVATION

RELATIONSHIP TO OTHER APPLICATIONS

This application claims the benefit of and priority to U.S. provisional application No. 61/623,211 filed 12 Apr. 2012 to the same inventors and assignee, titled "A method for preventing neoplastic transformation by inhibition of retinoblastoma protein inactivation".

STATEMENT OF SUPPORT

This invention was made with government support under National Cancer Institute Grant No. CA13268. The government has certain rights in the invention.

SEQUENCE LISTING

The information recorded in electronic form (if any) submitted (under Rule 13ter if appropriate) with this application is identical to the sequence listing as contained in the application as filed. A sequence listing text (.txt) file is submitted herewith under 37 CFR. 1.821(c) and is hereby incorporated by reference in its entirely. The details of the file as required under See 37 CFR. 1.52(e)(5) and 37 CFR 1.77(b)(5) are as follows: Name of file is SC2012_681_PCT_ST25.txt; date of creation is Saturday, Apr. 13, 2013; size is 4,982 bytes.

FIELD OF THE INVENTION

The field of the invention concerns mechanisms for cell cycle control, particularly inhibition of cell cycle progression into S phase by preventing the inactivation of Retinoblastoma protein (Rb), a cell cycle regulator protein that arrests cells in G1.

BACKGROUND

The Retinoblastoma protein is a nuclear phosphoprotein product of the RB 1 gene. It is. Retinoblastoma is a tumor suppressor because of its control over the cell cycle.

Unregulated cellular proliferation underlies neoplastic transformation and tumorigenesis. Tumor cells typically have acquired some genetic damage to the regulators of the cell cycle. The Retinoblastoma protein (Rb), is a cell cycle regulator protein that when active, arrests cells in G1. Rb orchestrates signals controlling of cell cycle progression, and cancer cells almost invariably have genetic alterations of Retinoblastoma protein (Rb) pathway components. Cyclin-dependent kinase (Cdk) phosphorylation of the Retinoblastoma protein (Rb) drives cell proliferation by inhibiting the formation of complexes between Rb and E2F transcription factors and other regulatory proteins. The mechanism of Rb inactivation is largely unknown.

Considering the high prevalence of Rb pathway lesions in cancer, there is clear motivation for therapeutics that target pathway components to inhibit aberrant proliferation.

BRIEF DESCRIPTION OF THE INVENTION

The present disclosure describes a method for preventing neoplastic transformation by inhibiting or downregulating the inactivation of Rb, whereby the method comprises preventing dissociation of the Rb-E2F complex or encouraging the formation of, or stabilization of, the Rb-E2F complex. The invention encompasses novel peptides that inhibit or downregulate Rb inactivation and thereby reduces cell proliferation and prevents neoplastic transformation.

GENERAL REPRESENTATIONS CONCERNING THE DISCLOSURE

All scientific papers, publications, patent documents and other disclosures mentioned herein and in any priority document are hereby incorporated by reference for all purposes.

The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features. This specification incorporates by reference all documents referred to herein and all documents filed concurrently with this specification or filed previously in connection with this application, including but not limited to such documents which are open to public inspection with this specification.

The term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

The term "fragment" refers to a part of a larger whole, for example a fragment of a molecule may be any dissociated part of that molecule, regardless of size.

The term "specie" or "group" when used to describe an "R" group in a chemical formula, is used to mean any chemical compound, sub-compound or substituent that may chemically interact with (covalently, ionically or by Van der Waal's forces) another molecule or group such as shown on a chemical formula.

When a "terminus" or "terminal group" is discussed as having a substituent, side-chain, group or moiety attached, that substituent, side-chain, group or moiety may equally be present at one or more termini or at side locations along the length of the molecule.

Peptide sequences are disclosed using the standard one or three letter code:

| Amino Acid    | 3-letter | 1-letter |
|---------------|----------|----------|
| Alanine       | Ala      | A        |
| Arginine      | Arg      | R        |
| Asparagine    | Asn      | N        |
| Aspartic acid | Asp      | D        |
| Cysteine      | Cys      | C        |
| Glutamic acid | Glu      | E        |
| Glutamine     | Gln      | Q        |
| Glycine       | Gly      | G        |
| Histidine     | His      | H        |
| Isoleucine    | Ile      | I        |
| Leucine       | Leu      | L        |
| Lysine        | Lys      | K        |
| Methionine    | Met      | M        |
| Phenylalanine | Phe      | F        |
| Proline       | Pro      | P        |
| Serine        | Ser      | S        |
| Threonine     | Thr      | T        |
| Tryptophan    | Trp      | W        |
| Tyrosine      | Tyr      | Y        |
| Valine        | Val      | V        |

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" or "minus" can refer to the antisense strand, and the designation "positive" or "plus" can refer to the sense strand.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of a parent sequence which is identical in sequence to but shorter in length than the parent sequence. A fragment may comprise up to the entire length of the defined sequence, minus one nucleotide/amino acid residue. For example, a fragment may be at least 5, 10, 15, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs. Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410). The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example: Matrix: BLOSUM62; Reward for match: 1; Penalty for mismatch: −2; Open Gap: 5 and Extension Gap: 2 penalties; Gap x drop-off: 50; Expect: 10; Word Size: 11; .Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the hydrophobicity and acidity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, Molecular Cloning: A Laboratory Manual, $2^{nd}$ ed., vol. 1-3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with the second nucleic acid sequence. For instance, a promoter is operably linked to a coding sequence if the promoter affects the transcription or expression of the coding sequence. Generally, operably linked DNA sequences may be in close proximity or contiguous and, where necessary to join two protein coding regions, in the same reading frame.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

A "conservatively substituted variant" of a peptide or protein is a peptide or protein as defined wherein one or more amino acid residues may have been conservatively substituted for another amino acid residue as shown in the table provided in this description.

"Conservative amino acid substitutions" are those substitutions that, when made, least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

DETAILED DESCRIPTION OF THE INVENTION

The Retinoblastoma Protein and Cell Cycle Regulation

Figure 1:
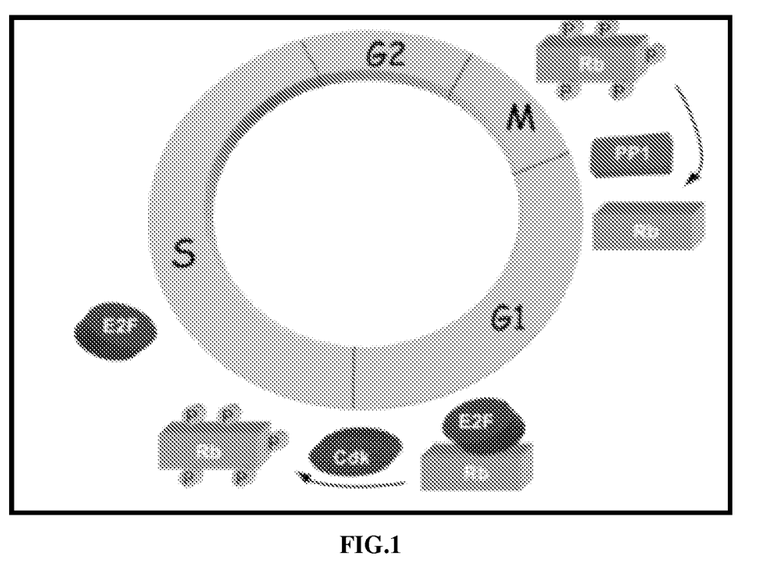
FIG. 1: Diagram of the mammalian cell cycle control of Rb by phosphorylation.

The mammalian cell cycle is commonly divided into four distinct phases termed G1, S, G2, and M (FIG. 1). DNA is replicated in S phase, and the contents of the cell are divided in mitosis (M phase). In late G1, cells pass through a "restriction point," after which they commit to entering S phase and proceed through division irrespective of whether further growth stimulation is received. The restriction point is regulated by a balance of growth-positive (e.g. mitogens) and growth-negative (e.g. cytokines) factors; these molecules initiate signalling cascades that converge on the retinoblastoma protein (Rb). Rb, through its effects on the transcription factor E2F and E2F-controlled genes, regulates the transcriptional program that initiates DNA synthesis (S phase). Inactivation of Rb or overexpression of E2F is sufficient to drive S phase whereas injection or expression of Rb arrests cells in G17-9. Thus, the protein components of the Rb-E2F pathway constitute the fundamental molecular machinery that coordinates proliferation signals with cell cycle progression.

Relevance of the Rb Pathway in Cancer and Cancer Therapeutics

Considering the high prevalence of Rb pathway lesions in cancer, there is clear motivation for therapeutics that target pathway components to inhibit aberrant proliferation. Unregulated cellular proliferation underlies tumorigenesis, and tumor cells typically have acquired some genetic damage to the regulators of the cell cycle. Whereas the Rb pathway orchestrates proper cellular signals with the mechanics of cell cycle progression, cancer cells almost invariably have genetic alterations of Rb pathway components, which allow them to proliferate despite proper signals. Rb, Cdk (Cyclins that inactivate Rb), and proteins that regulate Cdk activity are all commonly mutated in cancers from a diverse set of tissue types. The gene encoding Rb was in fact the first tumor suppressor gene cloned, and Rb is found mutated or deleted in retinoblastoma, a paediatric tumor of the retina that affects 1 in 20,000 live births, as well as in bladder and small cell lung carcinomas. Rb is also inactivated by oncogenic DNA viruses, which encode proteins that dissociate Rb-E2F complexes; a well-known example is the human papillomavirus virus (HPV) that causes the majority of cervical carcinomas.

The Cyclin D gene is amplified in oesophageal, squamous cell head and neck, and breast carcinomas as well as B cell lymphomas. The INK proteins, inhibitors of G1 Cdk activity, are found deleted in oesophageal squamous cell, lung, bladder, and pancreatic carcinomas and glioblastomas. In sum, the overwhelming presence of lesions in the Rb pathway in tumors of diverse tissue types has led many to believe that disruption of the pathway may be a prerequisite to uncontrolled proliferation and tumorigenesis.

As upregulated Cdk activity, achieved by overexpression of Cyclins or mutations in Cyclin-inhibitors, leads to loss of restriction point control via constitutive Rb phosphorylation, much effort has focused on design of therapeutic Cdk inhibitors. Several small molecule ATP-competitive inhibitors have been designed that efficiently inhibit Cdk activity in vitro; however, translation of these successes into viable drugs has been hampered by a lack of selectivity for specific Cdk kinase activity in vivo. Our invention of a molecule that directly binds Rb and prevents E2F release despite its phosphorylation is a novel approach towards inhibiting Rb inactivation.

Rb Structure and Mechanism of E2F Release

Figure 2:
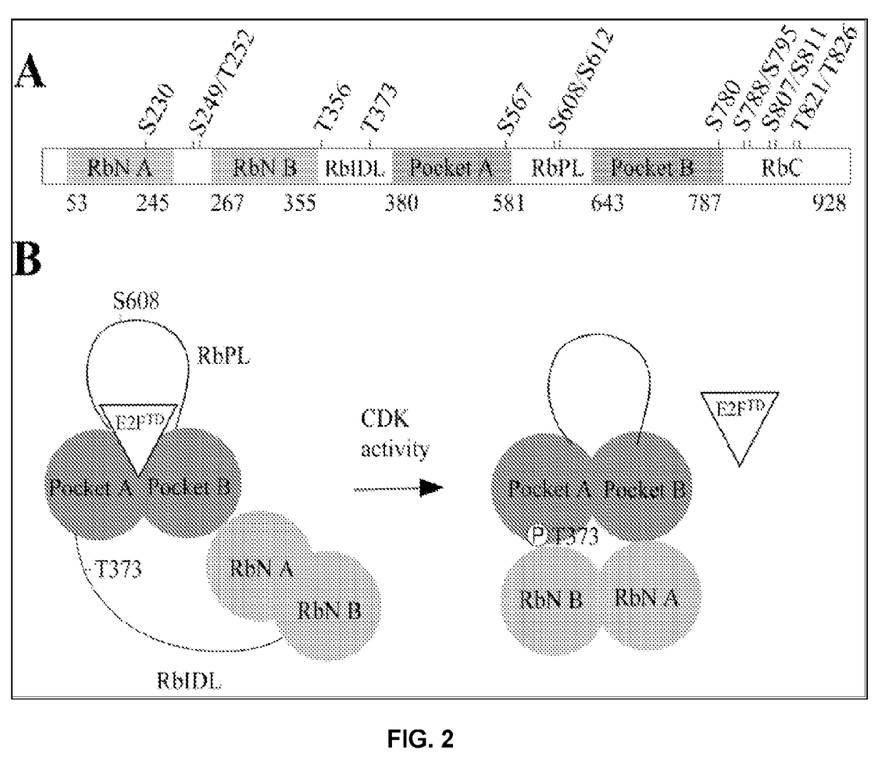
FIG. 2: (A) Domain structure of Rb and Cdk consensus sites. (B) Conformational change leading to E2F release.

Rb contains the RbN (the N-terminal domain), and pocket domains, and several intrinsically disordered regions: the interdomain linker between the two independently folded domains (RbIDL), the large loop within the pocket domain (RbPL), and the C-terminal domain (RbC) (FIG. 2A). Structures of isolated domains have been determined, however interdomain interactions and their relevance for Rb function are less well characterized. The Rb-E2F complex is stabilized primarily by an association between the E2F transactivation domain (E2FTD) and the Rb pocket domain. Cdk phosphorylation beginning in G1 occurs at thirteen consensus sites in unstructured regions of Rb, including RbIDL, RbPL, and RbC. The specific association between E2FTD and the pocket domain is inhibited by both T356/T373 phosphorylation in RbIDL and S608 phosphorylation in RbPL. The inventors recently characterized the structural effects of these phosphorylation events using x-ray crystallography and small angle x-ray scattering. The inventors found that T373 phoosphorylation produces a unique structural changes that result in allosteric and direct E2FTD inhibition (FIG. 2B).

Structure of inactive Rb: RbN Docking Weakens E2F Binding

Figure 4:
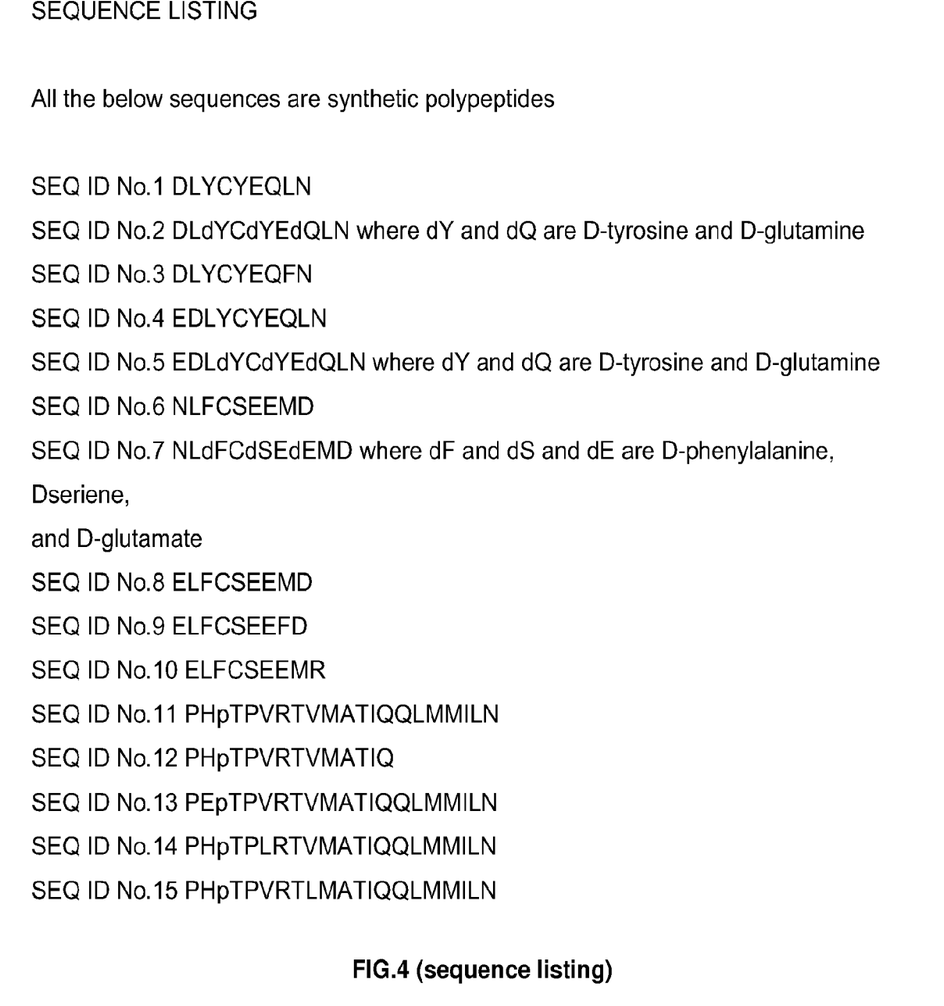
FIG. 4: Sequence listing showing the synthetic polypeptides defined by SEQ ID No. 1 to SEQ ID No. 15.

Our 2.7 Å crystal structure of T373 phosphorylated, inactive Rb reveals a closed conformation with RbN and the pocket associated across an extensive interface. The overall structures of the individual domains are similar to their structures observed in isolation; both contain two subdomains composed primarily of helical cyclin folds. The RbN-pocket interface is formed primarily between pocket subdomain A and RbN subdomain B and is mediated by T373 phosphorylation. The phosphothreonine sidechain forms an interdomain salt bridge with K164, which is found on the long helix (αN6) that connects the two RbN subdomains. The phosphate also makes an N-terminal helix capping interaction in the first helix of the pocket domain (αP1). The phosphate oxygens serve as hydrogen bond acceptors to backbone amide protons from R376 and V375 (FIG. 4B). This capping stabilizes αP1 such that two extra turns at its N-terminus are ordered relative to the unphosphorylated structure. These two turns position V375 and M379 to pack against RbN L161 and a conserved patch of hydrophobic residues (L212, V213 and F216), which were previously suggested to constitute a protein interaction surface in RbN. The C-terminal half of the αP1 helix packs against the pocket domain with residues I382 and L385 forming a hydrophobic interface with V494, T497, and Y498. In sum, T373 phosphorylation lengthens the αP1 helix and positions it to form an interface with RbN, holding both domains in the docked conformation.

Figure 3:
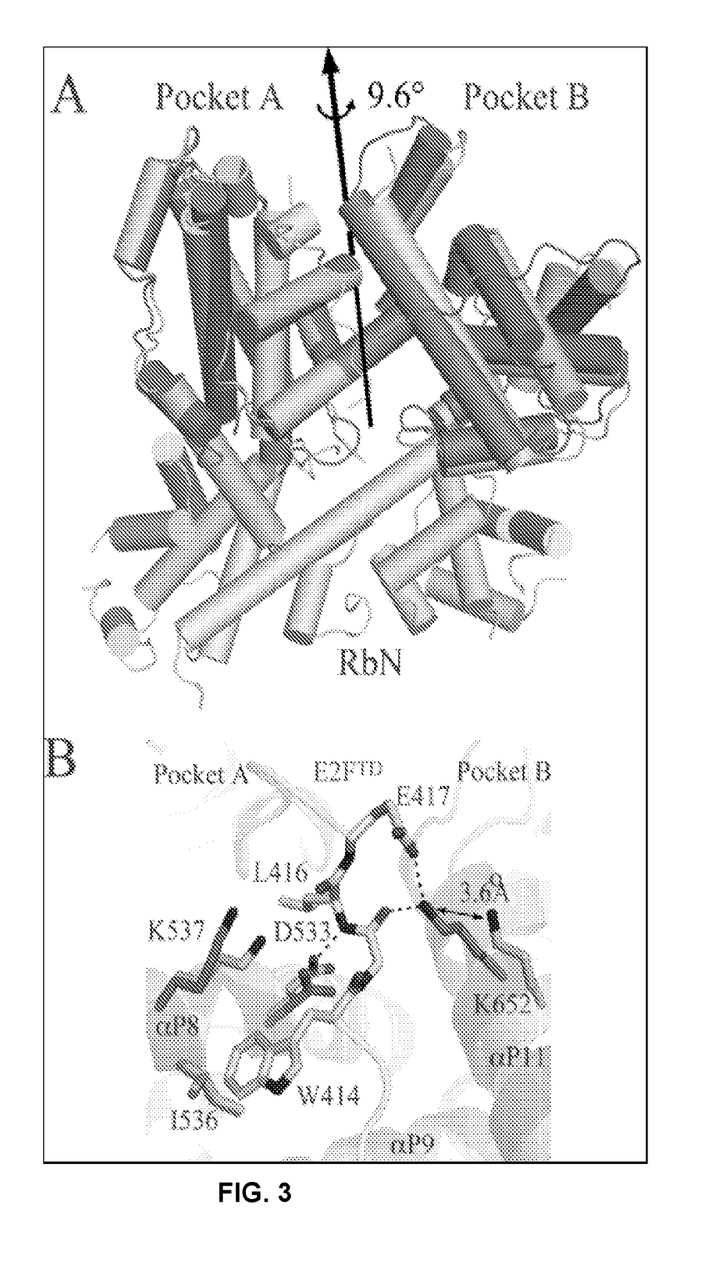
FIG. 3: (A) Structural comparison inactive Rb (gold and blue) with the E2FTD bound pocket domain (red). The pocket subdomain B of RbN-P is rotated by 9.6 degrees relative to the E2FTD-pocket subdomain B. (B) Close-up of the E2FTD binding cleft in the same structural alignment as in A. The subdomain orientation induced by RbN docking is incompatible with E2FTD binding.

Comparison of this inactive structure to structures of the pocket with E2F$^{TD}$ bound reveals that T373 phosphorylation inhibits E2F$^{TD}$ binding through an allosteric mechanism. RbN docking to the pocket induces a relative rotation of the pocket A and B subdomains by 9.6° about an axis that bisects them. To better visualize how this structural change is inconsistent with tight E2F$^{TD}$ binding, the inventors aligned the A subdomains of Rb$^{N-P}$ and the pocket-E2F$^{TD}$ structure (PDB: 1N4M) (FIG. 3). In this alignment, contacts between E2F$^{TD}$ and residues in pocket A of Rb$^{N-P}$ can be maintained, however distances to several residues in pocket B are too far for proper binding. For example, the sidechain amine of K652 is translated 3.6 Å away from its position in the pocket-E2F$^{TD}$ structure and is too distant to make its requisite interactions.

EMBODIMENTS OF THE INVENTION

The invention encompasses compositions and methods used to prevent E2F transcription factor release. The structural and binding data disclosed indicate that RbN-pocket association is critical for inhibition of E2F binding to the pocket domain. Conversely, the data indicate that inhibition of the RbN-pocket association should stabilize the growth-inhibitory Rb-E2F complex. This prediction is supported by the fact that Rb dephosphorylation, which would release RbN from the pocket domain, allows for E2F binding and cell cycle inhibition.

The invention encompasses a molecular inhibitor of RbN-pocket association, which can be used as a mechanism to arrest cells by trapping the suppressive Rb-E2F complex. This molecule binds to either the pocket or RbN domains and prevents their association. The molecule binds either the pocket or RbN domain but does not induce structural changes in the pocket that prevent E2F binding. The molecule allows E2F binding but does not allow RbN-pocket association, and therefore does not allow phosphorylation-dependent E2F release. The molecule therefore prevents Rb inactivation and E2F release despite phosphorylation of Rb. The molecule inhibits cell cycle progression by preventing Rb inactivation and E2F activation.

The invention specifically encompasses compounds or classes of compounds that act as inhibitors of retinoblastoma protein inactivation (see appendix No. 1 of manuscript, incorporated by reference). These include:

(i) A peptide or synthetic peptide mimetic corresponding to the "LxCxE" Rb binding motif found in viral and cellular proteins. Such mimetics include the LxCxE motif using the one letter amino acid code. The letter 'x' may be any amino acid. In some embodiments the amino acids L, C or E may be substituted conservatively (see 'Conservative amino acid substitutions'). In other embodiments any of the named amino acids may be substituted conservatively. Exemplary (but not limiting) species include:

```
                                            SEQ ID No. 1
DLYCYEQLN

SEQ ID No. 2
DLdYCdYEdQLN where dY and dQ are D-tyrosine
and D-glutamine

SEQ ID No. 3
DLYCYEQFN

SEQ ID No. 4
EDLYCYEQLN

SEQ ID No. 5
EDLdYCdYEdQLN where dY and dQ are D-tyrosine
and D-glutamine

SEQ ID No. 6
NLFCSEEMD

SEQ ID No. 7
NLdFCdSEdEMD where dF and dS and dE are
D-phenylalanine, D-seriene, and D-glutamate SEQ ID No. 8
ELFCSEEMD SEQ ID No. 9
ELFCSEEFD SEQ ID No. 10
ELFCSEEMR
```

(ii) A cyclic peptide that binds the "LxCxE" binding domain in the Rb pocket. The letter 'x' may be any amino acid. The letter 'x' may be any amino acid. In some embodiments any of the named amino acids may be substituted conservatively. Exemplary (but not limiting) species include:

```
                                            SEQ ID No. 11
PHpTPVRTVMATIQQLMMILN

SEQ ID No. 12
PHpTPVRTVMATIQ

SEQ ID No. 13
PEpTPVRTVMATIQQLMMILN

SEQ ID No. 14
PHpTPLRTVMATIQQLMMILN

SEQ ID No. 15
PHpTPVRTLMATIQQLMMILN
``` iii) A macrocycle natural product or small molecule from a chemical library that binds the "LxCxE" binding site in the Rb pocket domain.

iv) A peptide or synthetic peptide mimetic corresponding to the al helix in the Rb pocket domain.

v) A cyclic peptide that binds the al-binding site in the Rb N-terminal domain.

vi) A macrocycle natural product or small molecule from a chemical library that binds the al-binding site in the Rb N-terminal domain.

vii) Any compound that inhibits the interaction between the Rb pocket and Rb N-terminal domains.

Demonstration of proof of principle has been completed and compounds of the invention have proven to be successful inhibitors of Rb inactivation in vitro. The natural 'LxCxE' peptide prevents Rb inactivation by preventing the inhibition of E2F binding that otherwise occurs upon phosphorylation. Thus E2F sill binds to Rb despite phosphorylation.

The inventors have developed an assay for measuring the degree of binding between Rb and E2F. Rb inactivation corresponds to E2F binding inhibition. If you can prevent E2F binding to Rb, then you inactivate Rb, its tumor suppressing action decreases and the cell cycle continues from G1 to S and unregulated cell division occurs. Inactivation occurs upon Rb phosphorylation by Cdk. The inventors have discovered that in the presence of 'LxCxE' peptide, E2F inhibition is prevented upon phosphorylation. The applicant's structural work suggests this occurs because the binding of the 'LxCxE' peptide blocks association between the Rb pocket and Rb N-terminal domains that is required for E2F inhibition.

The exemplary compound used to demonstrate the invention is the peptide DLYCYEQLN. The experiment was carried out as follows.

Materials:

The DLYCYEQLN peptide was made synthetically using standard peptide synthesis. Human E2F1 transactivation domain (residues 380-727) and a human Rb construct (residues 53-787, delta245-267, delta582-642, S780A) were produced recombinantly in E. coli and purified to homogeneity. Rb was phosphorylated with recombinant Cdk as described.

Methods:

Rb activity, defined as its ability to bind E2F, was assayed by isothermal titration calorimetry to measure quantitatively E2F binding affinity. About 50 micromolar (μm) Rb was used in the calorimetry cell and E2F was titrated in at a concentration of ~1 mM. Standard protocols were used to determine Kd. In the experiment with the DLYCYEQLN peptide, the peptide was first added to the cell before E2F to saturate Rb. The inventors then compared E2F affinity for un-phosphorylated (active) Rb, phosphorylated (inactive) Rb, and phosphorylated Rb in the presence of the DLYCYEQLN peptide.

Results/Conclusion:

The applicant found that by comparing E2F binding to un-phosphorylated and phosphorylated Rb that phosphorylation at T373 in Rb (sufficient for Rb inactivation in cells) reduces the E2F affinity from Kd~100 nM to Kd~3 μM. In the presence of the DLYCYEQLN peptide, however, phosphorylation of Rb only reduces the E2F affinity to Kd~700 nM. The inventors conclude that the DLYCYEQLN peptide inhibits the weakening effect of phosphorylation on E2F-Rb binding, and thereby inhibits Rb inactivation.

FURTHER EMBODIMENTS AND EXAMPLES

Additionally, the inventors provide further proof of concept, deriving structures of phosphorylated Rb that reveal the mechanism of its inactivation. See Burke J R, Hura G L, Rubin S M. Genes Dev. 2012 Jun. 1; 26(11):1156-66. doi: 10.1101/gad.189837.112. E-pub 2012 May 8. Structures of inactive retinoblastoma protein reveal multiple mechanisms for cell cycle control.

S608 phosphorylation orders a flexible "pocket" domain loop such that it mimics and directly blocks E2F transactivation domain (E2FTD) binding. T373 phosphorylation induces a global conformational change that associates the pocket and N-terminal domains (RbN). This first multidomain Rb structure demonstrates a novel role for RbN in allosterically inhibiting the E2FTD-pocket association and protein binding to the pocket LxCxE site. Together these structures detail the regulatory mechanism for a canonical growth repressive complex and provide a novel example of how multisite Cdk phosphorylation induces diverse structural changes to influence cell cycle signaling. The results demonstrate the phosphorylation-induced structural changes in Rb that result in loss of E2F affinity. The crystal structures specifically implicate T373 and 5608 as the key phosphorylation events for E2FTD inhibition.

These observations are consistent with assays for E2F binding and Rb inactivation in cancer cell models that found critical phosphorylation events in RbPL and RbIDL. In particular, the importance of T373 phosphorylation in the mechanism of Rb inactivation is supported by the observation that only T373 phosphorylation is sufficient for E2F dissociation and activation in cells (Lents et al. 2006; Gorges et al. 2008). The RbN-P structure and SAXS data also explain the critical role for RbN in Rb inactivation previously suggested by cellular assays (Knudsen and Wang 1997). RbN docking to the pocket, which is stimulated by T373 phosphorylation, induces a change in the relative pocket subdomain orientation that perturbs the E2F binding site. The inventors found that T373 and 5608 phosphorylation induce remarkably distinct structures and mechanisms for E2F inhibition.

The independence of the two mechanisms explains how cumulative Rb phosphorylation synergistically induces Rb-E2F inhibition and E2F activation (Burke et al. 2010; Brown et al. 1999); both mechanisms can simultaneously reduce E2F affinity. At the same time, the differences in the mechanisms offer new insights into the importance of diverse phosphorylation pathways leading to Rb inactivation. It is noteworthy that phosphorylated RbPL directly competes with E2FTD for pocket binding, while phosphorylation-induced RbN docking weakens E2FTD affinity through an allosteric interaction. Direct RbPL competition for binding is an efficient mechanism for inhibiting E2F complex formation, but likely not for dislodging E2F that is already tightly bound. The allosteric mechanism, in which phosT373-induced RbN docking opens the E2F binding site, is better suited for dissociating preformed Rb-E2F complexes. Thus, distinct mechanisms for E2F inhibition may be relevant and employed depending on the particular cellular context.

Interestingly, the observation of an allosteric interaction mediating E2F release suggests the possibility of therapeutically targeting the RbN-pocket interface to prevent Rb inactivation. The particular Rb conformations that result from distinct phosphorylation events also differ in their ability to bind other protein factors. The applicants found here that in addition to reducing E2F affinity, T373 phosphorylation uniquely inhibits binding at the LxCxE site. The applicants propose that an additional important role for multisite phosphorylation in E2F inhibition is that distinct phosphorylations differentially modulate other Rb complexes. This function of multisite phosphorylation in cell cycle signaling is novel compared to previous well characterized examples, in which the enzymatic mechanism of multisite phosphorylation tune the signaling properties of a single output (Koivomagi et al.; Nash et al. 2001; Kim and Ferrell 2007). Here, the structural diversity of different Rb phosphoforms supports a model in which multisite Cdk phosphorylation generates multiple signaling outputs by assembling distinct protein complexes.

In summary, the present disclosure describes a method for preventing neoplastic transformation by inhibiting or downregulating the inactivation of Rb, whereby the method comprises preventing dissociation of the Rb-E2F complex or encouraging the formation of, or stabilization of, the Rb-E2F complex. The invention encompasses novel peptides that inhibit or downregulate Rb inactivation and thereby reduces cell proliferation and prevents neoplastic transformation.

REFERENCES

1. Pardee, A. B. G1 events and regulation of cell proliferation. Science 246, 603-8 (1989).

2. Weinberg, R. The retinoblastoma protein and cell cycle control. Cell 81, 323-30 (1995).
3. Dyson. The regulation of E2F by pRB-family proteins. Genes Dev 12, 2245-62 (1998).
4. Trimarchi. Sibling rivalry in the E2F family. Nat Rev Mol Cell Biol 3, 11-20 (2002).
5. Qin, X. Q., et al. Deregulated transcription factor E2F-1 expression leads to S-phase entry and p53-mediated apoptosis. Proc Natl Acad Sci USA 91, 10918-22 (1994).
6. Johnson, et al. Expression of transcription factor E2F1 induces quiescent cells to enter S phase. Nature 365, 349-52 (1993).
7. Goodrich, D. et al. The retinoblastoma gene product regulates progression through the G1 phase of the cell cycle. Cell 67, 293-302 (1991).
8. Huang, H. J. et al. Suppression of the neoplastic phenotype by replacement of the RB gene in human cancer cells. Science 242, 1563-6 (1988).
9. Qin, X. Q. et al. Identification of a growth suppression domain within the retinoblastoma gene product. Genes Dev 6, 953-64 (1992).
10. Adams, P. D. Regulation of the retinoblastoma tumor suppressor protein by cyclin/cdks. Biochim Biophys Acta 1471, M123-33 (2001).
11. Buchkovich, K., et al. The retinoblastoma protein is phosphorylated during specific phases of the cell cycle. Cell 58, 1097-105 (1989).
12. Chen, P. et al. Phosphorylation of the retinoblastoma gene product is modulated during the cell cycle and cellular differentiation. Cell 58, 1193-8 (1989).
13. Ludlow, J. W. et al. A. Specific enzymatic dephosphorylation of the retinoblastoma protein. Mol Cell Biol 13, 367-72 (1993).
14. Ludlow, J. W., Shon, J., Pipas, J. M., Livingston, D. M. & DeCaprio, J. A. The retinoblastoma susceptibility gene product undergoes cell cycle-dependent dephosphorylation and binding to and release from SV40 large T. Cell 60, 387-96 (1990).
15. Tamrakar, S., et al. Role of pRB dephosphorylation in cell cycle regulation. Front Biosci 5, D121-37 (2000).
16. Chellappan, S. et al. The E2F transcription factor is a cellular target for the RB protein. Cell 65, 1053-61 (1991).
17. Fattaey, A., Helin, K. & Harlow, E. Transcriptional inhibition by the retinoblastoma protein. Philos Trans R Soc Lond B Biol Sci 340, 333-6 (1993).
18. Flemington, E. K., Speck, S. H. & Kaelin, W. G., Jr. E2F-1-mediated transactivation is inhibited by complex formation with the retinoblastoma susceptibility gene product. Proc Natl Acad Sci USA 90, 6914-8 (1993).
19. Hiebert, S. et al. The interaction of RB with E2F coincides with an inhibition of the transcriptional activity of E2F. Genes Dev 6, 177-85 (1992).
20. Brehm, A. et al. Retinoblastoma protein recruits histone deacetylase to repress transcription. Nature 391, 597-601 (1998).
21. Kennedy, B. K. et al. Histone deacetylase-dependent transcriptional repression by pRB in yeast occurs independently of interaction through the LXCXE binding cleft. Proc Natl Acad Sci USA 98, 8720-5 (2001).
22. Nielsen, S. J. et al. Rb targets histone H3 methylation and HP1 to promoters. Nature 412, 561-5 (2001).
23. Weintraub, S. J., et al. Mechanism of active transcriptional repression by the retinoblastoma protein. Nature 375, 812-815 (1995).
24. Zhang, H. S. et al. Exit from G1 and S phase of the cell cycle is regulated by repressor complexes containing HDAC-Rb-hSWI/SNF and Rb-hSWI/SNF. Cell 101, 79-89 (2000).
25. Lees, J. et al. The retinoblastoma protein is phosphorylated on multiple sites by human cdc2. Embo J 10, 4279-90 (1991).
26. Hinds, P. W. et al. Regulation of retinoblastoma protein functions by ectopic expression of human cyclins. Cell 70, 993-1006 (1992).
27. Brown, V. D., Phillips, R. A. & Gallie, B. L. Cumulative effect of phosphorylation of pRB on regulation of E2F activity. Mol Cell Biol 19, 3246-56 (1999).
28. Harbour, J. et al. Cdk phosphorylation triggers sequential intramolecular interactions that progressively block Rb functions as cells move through G1. Cell 98, 859-69 (1999).
29. Knudsen, E. S. & Wang, J. Y. Dual mechanisms for the inhibition of E2F binding to RB by cyclin-dependent kinase-mediated RB phosphorylation. Mol Cell Biol 17, 5771-83 (1997).
30. Lundberg, A. et al. Functional inactivation of the retinoblastoma protein requires sequential modification by at least two distinct cyclin-cdk. Mol Cell Biol 18, 753-61 (1998).
31. Malumbres, M. & Barbacid, M. To cycle or not to cycle: a critical decision in cancer. Nat Rev Cancer 1, 222-31 (2001).
32. Shen, C. J. Cancer cell cycles. Science 274, 1672-7 (1996).
33. Classon, M. & Harlow, E. The retinoblastoma tumour suppressor in development and cancer. Nat Rev Cancer 2, 910-7 (2002).
34. Friend, S. H. et al. A human DNA segment with properties of the gene that predisposes to retinoblastoma and osteosarcoma. Nature 323, 643-6 (1986).
35. Horowitz, J. M. et al. Frequent inactivation of the retinoblastoma anti-oncogene is restricted to a subset of human tumor cells. Proc Natl Acad Sci USA 87, 2775-9 (1990).
36. Knudson, A. G., Jr. Mutation and cancer: statistical study of retinoblastoma. Proc Natl Acad Sci USA 68, 820-3 (1971).
37. Dyson, N., Howley, P. M., Munger, K. & Harlow, E. The human papilloma virus-16 E7 oncoprotein is able to bind to the retinoblastoma gene product. Science 243, 934-7 (1989).
38. zur Hausen, H. Viruses in human cancers. Science 254, 1167-73 (1991).
39. Hunter, T. & Pines, J. Cyclins and cancer. II: Cyclin D and CDK inhibitors come of age. Cell 79, 573-82 (1994).
40. Hall, M. & Peters, G. Genetic alterations of cyclins, cyclin-dependent kinases, and Cdk inhibitors in human cancer. Adv Cancer Res 68, 67-108 (1996).
41. Kamb, A. et al. A cell cycle regulator potentially involved in genesis of many tumor types. Science 264, 436-40 (1994).
42. Hirai, H., Kawanishi, N. & Iwasawa, Y. Recent advances in the development of selective small molecule inhibitors for cyclin-dependent kinases. Curr Top Med Chem 5, 167-79 (2005).
43. Hassler, M. et al. Crystal structure of the retinoblastoma protein N domain provides insight into tumor suppression, ligand interaction, and holoprotein architecture. Mol Cell 28, 371-85 (2007).
44. Lee, J. O., Russo, A. A. & Pavletich, N. P. Structure of the retinoblastoma tumour-suppressor pocket domain bound to a peptide from HPV E7. Nature 391, 859-65 (1998).

45. Rubin, S. M., Gall, A. L., Zheng, N. & Pavletich, N. P. Structure of the Rb C-terminal domain bound to E2F1-DP1: a mechanism for phosphorylation-induced E2F release. Cell 123, 1093-106 (2005).
46. Lee, C., Chang, J. H., Lee, H. S. & Cho, Y. Structural basis for the recognition of the E2F transactivation domain by the retinoblastoma tumor suppressor. Genes Dev 16, 3199-212 (2002).
47. Xiao, B. et al. Crystal structure of the retinoblastoma tumor suppressor protein bound to E2F and the molecular basis of its regulation. Proc Natl Acad Sci USA 100, 2363-8 (2003).
48. Zarkowska, T. & Mittnacht, S. Differential phosphorylation of the retinoblastoma protein by G1/S cyclin-dependent kinases. J Biol Chem 272, 12738-46 (1997).
49. Burke, J. R., Deshong, A. J., Pelton, J. G. & Rubin, S. M. Phosphorylation-induced conformational changes in the retinoblastoma protein inhibit E2F transactivation domain binding. J Biol Chem 285, 16286-93.
50. Burke J R, Hura G L, Rubin S M. Genes Dev. 2012 Jun. 1; 26(11):1156-66. doi: 10.1101/gad. 189837.112. E-pub 2012 May 8. Structures of inactive retinoblastoma protein reveal multiple mechanisms for cell cycle control.

The invention claimed is:

1. A synthetic peptide for the reduction of cell proliferation that inhibits cell cycle progression into S phase by stabilizing the Rb-E2F complex, wherein the synthetic peptide comprises an LxCxE motif is selected from the group consisting of:

```
                                                    SEQ ID No. 2
DLdYCdYEdQLN where dY and dQ are D-tyrosine
and D-glutamine SEQ ID No. 4
EDLYCYEQLN SEQ ID No. 5
EDLdYCdYEdQLN where dY and dQ are D-tyrosine
and D-glutamine SEQ ID No. 7
NLdFCdSEdEMD where dF and dS and dE are
D-phenylalanine, D-seriene, and D-glutamate SEQ ID No. 8
ELFCSEEMD SEQ ID No. 9
ELFCSEEFD
and SEQ ID No. 10
ELFCSEEMR,
``` wherein the amino acids L, C or E in the LxCxE motif, in the above sequences may be substituted conservatively.

2. The synthetic peptide of claim 1 selected from the group consisting of:

```
                                                    SEQ ID No. 2
DLdYCdYEdQLN where dY and dQ are D-tyrosine
and D-glutamine SEQ ID No. 4
EDLYCYEQLN SEQ ID No. 5
EDLdYCdYEdQLN where dY and dQ are D-tyrosine
and D-glutamine SEQ ID No. 7
NLdFCdSEdEMD where dF and dS and dE are
D-phenylalanine, D-seriene, and D-glutamate
```

-continued

```
                        SEQ ID No. 8
ELFCSEEMD

SEQ ID No. 9
ELFCSEEFD

SEQ ID No. 10
ELFCSEEMR.
```

3. The synthetic peptide of claim 1 selected from the group consisting of:

```
                                SEQ ID No. 2
DLdYCdYEdQLN where dY and dQ are D-tyrosine
and D-glutamine SEQ ID No. 5
EDLdYCdYEdQLN where dY and dQ are D-tyrosine
and D-glutamine and SEQ ID No. 7
NLdFCdSEdEMD where dF and dS and dE are
D-phenylalanine, D-seriene, and D-glutamate.
```

\* \* \* \* \*

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide, Molecular Inhibitor

<400> SEQUENCE: 1

Asp Leu Tyr Cys Tyr Glu Gln Leu Asn
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide, Molecular Inhibitor
<220> FEATURE:
<221> NAME/KEY: misc_feature
<222> LOCATION: (3)..(3)
<223> OTHER INFORMATION: Xaa is D-tyrosine
<220> FEATURE:
<221> NAME/KEY: misc_feature
<222> LOCATION: (5)..(5)
<223> OTHER INFORMATION: Xaa is D-tyrosine
<220> FEATURE:
<221> NAME/KEY: misc_feature
<222> LOCATION: (7)..(7)
<223> OTHER INFORMATION: Xaa is D-glutamine

<400> SEQUENCE: 2

Asp Leu Xaa Cys Xaa Glu Xaa Leu Asn
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide, Molecular Inhibitor

<400> SEQUENCE: 3

Asp Leu Tyr Cys Tyr Glu Gln Phe Asn
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide, Molecular Inhibitor
```

<400> SEQUENCE: 4

Glu Asp Leu Tyr Cys Tyr Glu Gln Leu Asn
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide, Molecular Inhibitor
<220> FEATURE:
<221> NAME/KEY: misc_feature
<222> LOCATION: (4)..(4)
<223> OTHER INFORMATION: Xaa is D-tyrosine
<220> FEATURE:
<221> NAME/KEY: misc_feature
<222> LOCATION: (6)..(6)
<223> OTHER INFORMATION: Xaa is D-tyrosine
<220> FEATURE:
<221> NAME/KEY: misc_feature
<222> LOCATION: (8)..(8)
<223> OTHER INFORMATION: Xaa is D-glutamine

<400> SEQUENCE: 5

Glu Asp Leu Xaa Cys Xaa Glu Xaa Leu Asn
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide, Molecular Inhibitor

<400> SEQUENCE: 6

Asn Leu Phe Cys Ser Glu Glu Met Asp
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide, Molecular Inhibitor
<220> FEATURE:
<221> NAME/KEY: misc_feature
<222> LOCATION: (3)..(3)
<223> OTHER INFORMATION: Xaa is D-phenylalanine
<220> FEATURE:
<221> NAME/KEY: misc_feature
<222> LOCATION: (5)..(5)
<223> OTHER INFORMATION: Xaa is D-serine
<220> FEATURE:
<221> NAME/KEY: misc_feature
<222> LOCATION: (7)..(7)
<223> OTHER INFORMATION: Xaa is D-glutamate

<400> SEQUENCE: 7

Asn Leu Xaa Cys Xaa Glu Xaa Met Asp
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide, Molecular Inhibitor -continued

<400> SEQUENCE: 8

Glu Leu Phe Cys Ser Glu Glu Met Asp
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide, Molecular Inhibitor

<400> SEQUENCE: 9

Glu Leu Phe Cys Ser Glu Glu Phe Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide, Molecular Inhibitor

<400> SEQUENCE: 10

Glu Leu Phe Cys Ser Glu Glu Met Arg
1               5

<210> SEQ ID NO 11
<211> LENGTH: 20
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: PHOSPHORYLATION
<220> FEATURE:
<223> OTHER INFORMATION: Synthetic Peptide, Molecular Inhibitor

<400> SEQUENCE: 11

Pro His Thr Pro Val Arg Thr Val Met Ala Thr Ile Gln Gln Leu Met
1               5                   10                  15

Met Ile Leu Asn
            20

<210> SEQ ID NO 12
<211> LENGTH: 13
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: PHOSPHORYLATION
<220> FEATURE:
<223> OTHER INFORMATION: Synthetic Peptide, Molecular Inhibitor

<400> SEQUENCE: 12

Pro His Thr Pro Val Arg Thr Val Met Ala Thr Ile Gln
1               5                   10

<210> SEQ ID NO 13
<211> LENGTH: 20
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: PHOSPHORYLATION
<220> FEATURE:
<223> OTHER INFORMATION: Synthetic Peptide, Molecular Inhibitor

```
<400> SEQUENCE: 13

Pro Glu Thr Pro Val Arg Thr Val Met Ala Thr Ile Gln Gln Leu Met
1               5                   10                  15

Met Ile Leu Asn
            20

<210> SEQ ID NO 14
<211> LENGTH: 20
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: PHOSPHORYLATION
<220> FEATURE:
<223> OTHER INFORMATION: Synthetic Peptide, Molecular Inhibitor

<400> SEQUENCE: 14

Pro His Thr Pro Leu Arg Thr Val Met Ala Thr Ile Gln Gln Leu Met
1               5                   10                  15

Met Ile Leu Asn
            20

<210> SEQ ID NO 15
<211> LENGTH: 20
<212> TYPE: PRT
<213> ORGANISM: Artificial Sequence
<220> FEATURE:
<221> NAME/KEY: MOD_RES
<222> LOCATION: (3)..(3)
<223> OTHER INFORMATION: PHOSPHORYLATION
<220> FEATURE:
<223> OTHER INFORMATION: Synthetic Peptide, Molecular Inhibitor

<400> SEQUENCE: 15

Pro His Thr Pro Val Arg Thr Leu Met Ala Thr Ile Gln Gln Leu Met
1               5                   10                  15

Met Ile Leu Asn
            20
```